(12) United States Patent
Tourrasse et al.

(10) Patent No.: US 10,982,237 B2
(45) Date of Patent: Apr. 20, 2021

(54) MICROBIAL CONSORTIUM FOR 1,3-PROPANEDIOL PRODUCTION USING HIGH GLYCEROL CONCENTRATION

(71) Applicant: METABOLIC EXPLORER, Saint Beauzire (FR)

(72) Inventors: Olivier Tourrasse, Les Martres de Veyre (FR); Céline Raynaud, Saint-Beauzire (FR)

(73) Assignee: METABOLIC EXPLORER, Saint Beauzire (FR)

( * ) Notice: Subject to any disclaimer, the term of this patent is extended or adjusted under 35 U.S.C. 154(b) by 0 days.

(21) Appl. No.: 16/478,777

(22) PCT Filed: Feb. 19, 2018

(86) PCT No.: PCT/EP2018/054018
§ 371 (c)(1),
(2) Date: Jul. 17, 2019

(87) PCT Pub. No.: WO2018/150023
PCT Pub. Date: Aug. 23, 2018

(65) Prior Publication Data
US 2019/0352678 A1 Nov. 21, 2019

(30) Foreign Application Priority Data
Feb. 20, 2017 (EP) .................................... 17305187

(51) Int. Cl.
C12P 7/18 (2006.01)
C12N 1/20 (2006.01)

(52) U.S. Cl.
CPC . *C12P 7/18* (2013.01); *C12N 1/20* (2013.01)

(58) Field of Classification Search
None
See application file for complete search history.

(56) References Cited

U.S. PATENT DOCUMENTS

| 8,236,994 B2 * | 8/2012 | Soucaille | C12N 9/1029 568/852 |
| 2003/0175916 A1 | 9/2003 | Sarcabal et al. | |
| 2010/0028965 A1 | 2/2010 | Liu et al. | |

FOREIGN PATENT DOCUMENTS

| WO | WO 01/04324 A1 | 1/2001 |
| WO | WO 2006/128381 A1 | 12/2006 |
| WO | WO 2008/040387 A1 | 4/2008 |
| WO | WO 2009/068110 A1 | 6/2009 |
| WO | WO 2010/037843 A1 | 4/2010 |
| WO | WO 2010/046928 A2 | 4/2010 |
| WO | WO 2010/128070 A2 | 11/2010 |
| WO | WO 2011/042434 A1 | 4/2011 |
| WO | WO 2012/062832 A1 | 5/2012 |

OTHER PUBLICATIONS

European Search Report dated Jul. 31, 2017, for European Application No. 17305187.
González-Pajuelo et al., "Metabolic engineering of Clostridium acetobutylicum for the industrial production of 1,3-propanediol from glycerol", Metabolic Engineering, vol. 7, 2005, pp. 329-336.
González-Pajuelo et al., "Microbial Conversion of Glycerol to 1,3-Propanediol: Physiological Comparison of a Natural Producer, Clostridium butyricum VPI 3266, and an Engineered Strain, Clostridium acetobutylicum DG1(pSPD5)", Applied and Environmental Microbiology, vol. 72 No. 1, Jan. 2006 pp. 96-101.
International Search Report dated Jun. 6, 2018, for International Application No. PCT/EP2018/054018.
Papanikolaou et al., "High production of 1,3-propanediol from industrial glycerol by a newly isolated Clostridium butyricum strain", Journal of Biotechnology, vol. 77, 2000, pp. 191-208.
Quéméneur et al., "Changes in hydrogenase genetic diversity and proteomic patterns in mixed-culture dark fermentation of mono-, di- and tri-saccharides", International Journal of Hydrogen Energy, vol. 36, No. 18, Jul. 20, 2011, pp. 11654-11665.
Quéméneur et al., "Functional versus phylogenetic fingerprint analyses for monitoring hydrogen-producing bacterial populations in dark fermentation cultures", International Journal of Hydrogen Energy, vol. 36, No. 6, Dec. 18, 2010, pp. 3870-3879.
Tran-Din et al., "Formation of $_D(-)$-1,2-propanediol and $D(-)$-lactate from glucose by Clostridium sphenoides under phosphate limitation", Archives of Microbiology, vol. 142, 1985, pp. 87-92.
Vasconcelos et al., "Regulation of carbon and electron flow in Clostridium acetobutylicum grown in chemostat culture at neutral pH on mixtures of glucose and glycerol", Journal of Bacteriology, vol. 176, No. 3, Mar. 1994, pp. 1443-1450.

* cited by examiner

Primary Examiner — Anand U Desai
(74) Attorney, Agent, or Firm — Birch, Stewart, Kolasch & Birch, LLP

(57) ABSTRACT

The present invention relates to a microbial consortium, especially adapted for growth and production of 1,3-propanediol from a culture medium with high glycerinecontent and specifically with a high concentration of industrial glycerine. More particularly, this microbial consortium comprises at least one strain *C. acetobutylicum* and at least one strain chosen among strains of *C. sporogenes* and/or strains of *C. sphenoides*. The invention also relates to a method for the production of 1,3-propanediol by culturing this microbial consortium resulting in a co-culture of these particular different microorganisms.

14 Claims, No Drawings
Specification includes a Sequence Listing.

MICROBIAL CONSORTIUM FOR 1,3-PROPANEDIOL PRODUCTION USING HIGH GLYCEROL CONCENTRATION

The present invention relates to a microbial consortium, especially adapted for growth and production of 1,3-propanediol from a culture medium with high glycerol content and specifically with a high concentration of glycerol originating from industrial glycerine. More particularly, this microbial consortium comprises at least one strain *Clostridium acetobutylicum* and at least one strain chosen among strains of *Clostridium sporogenes* and/or strains of *Clostridium sphenoides*. The invention also relates to a method for the production of 1,3-propanediol by culturing this microbial consortium resulting in a co-culture of these particular different microorganisms.

BACKGROUND OF THE INVENTION 1,3-propanediol (PDO), also called trimethylene glycol or propylene glycol, is one of the oldest known fermentation products. It was originally identified as early as 1881 by August Freund in a glycerine fermented culture containing *Clostridium pasteurianum*. PDO is a typical product of glycerine fermentation and has been found in anaerobic conversions of other organic substrates. Only very few organisms, all of them bacteria, are able to form it. They include enterobacteria of the genera *Klebsiella* (*K. pneumoniae*), *Enterobacter* (*E. agglomerans*) and *Citrobacter* (*C. freunddi*), *Lactobacilli* (*L. brevis* and *L. buchneri*) and *Clostridia* of the *C. butyricum* and the *C. pasteurianum* group.

PDO, as a bifunctional organic compound, may potentially be used for many synthesis reactions, in particular as a monomer for polycondensations to produce polyesters, polyethers, polyurethanes, and in particular, polytrimethylene terephtalate (PTT). These structure and reactivity features lead to several applications in cosmetics, textiles (clothing fibers or flooring) or plastics (car industry and packing or coating).

PDO can be produced by different chemical routes but they generate waste stream containing extremely polluting substances and the cost of production is high. Thus, chemically produced PDO cannot compete with the petrochemically available diols like 1,2-ethanediol, 1,2-propanediol and 1,4-butanediol. To increase this competitiveness, in 1995, DuPont started a research program for the biological conversion of glucose to PDO. Although this process is environmentally friendly it has the disadvantage to i) use vitamin B12 a very expensive cofactor and ii) be a discontinuous process due to the instability of the producing strain.

Due to the availability of large amounts of glycerol produced by the bio-diesel industry, a continuous, vitamin-B12-free process with a higher carbon yield would on the contrary, be advantageous.

It is known in the art that PDO can be produced from glycerine, an unwanted by-product in particular from the biodiesel production that contains roughly 80-85% of glycerol mixed with salts and water.

*C. butyricum* was previously described as being able to grow and produce PDO from glycerol contained in industrial glycerine in batch and two-stage continuous fermentation (Papanikolaou et al., 2000). However, at the highest glycerol concentration, the maximal PDO titer obtained was 48.1 g·L$^{-1}$ at a dilution rate of 0.02 h$^{-1}$, meaning a productivity of 0.96 g·L$^{-1}$·h$^{-1}$. The cultures were conducted with a maximum concentration of glycerol originating from glycerine in the fed medium of 90 g·L$^{-1}$ and in the presence of yeast extract, a costly compound containing organic nitrogen that is known by the man skilled in the art to help increase bacterial biomass production.

Application WO 2006/128381 discloses the use of this glycerol for the production of PDO with batch and fed-batch cultures using natural PDO producing organisms such as *Klebsiella pneumoniae*, *C. butyricum* or *C. pasteurianum*. Furthermore, the medium used in WO 2006/128381 also contains yeast extract. As described in this patent application, the maximal productivity reached was comprised between 0.8 and 1.1 g.

The performance of a *C. acetobutylicum* strain modified to contain the vitamin B12-independent glycerine-dehydratase and the PDO-dehydrogenase from *C. butyricum*, called "*C. acetobutylicum* DG1 pSPD5" strain has been described in Gonzalez-Pajuelo et al., 2005. This strain originally grows and produces PDO in a fed medium containing up to 120 g·l$^{-1}$ of pure glycerol. In addition, analyses in a fed medium containing a maximum of 60 g·l$^{-1}$ of pure glycerol or glycerol contained in industrial glycerine did not point out to any differences. These results have been obtained in presence of yeast extract. Moreover, no test was performed with concentrations of glycerol originating from industrial glycerine higher than 60 g·l$^{-1}$. When comparing a wild-type *C. butyricum* to the modified microorganism "*C. acetobutylicum* DG1 pSPD5", a globally similar behaviour was observed.

In patent application WO 2010/128070 the inventors described a process to adapt the strain of *C. acetobutylicum* DG1 pSPD5 such as described in Gonzalez-Pajuelo et al. (2005) to grow in a medium with a high concentration of glycerol contained in industrial glycerine and without yeast extract. The resulting population of *C. acetobutylicum* DG1 pSPD5 adapted strains was able to produce PDO in medium containing up to 120 g·l$^{-1}$ of glycerol contained in industrial glycerine with a titer up to 53.5 g·L$^{-1}$ of PDO, a yield up to 0.53 g·g$^{-1}$ and productivity up to 2.86 g·L$^{-1}$·h$^{-1}$. In patent application WO 2012/062832, the inventors described the isolation of clone from another population of *C. acetobutylicum* DG1 pSPD5 adapted strains obtained by the same process as described in WO 2010/128070 patent application. This second population was able to produce PDO in medium containing around 105 g·L$^{-1}$ of glycerol contained in industrial glycerine with a titer up to 50.45 g/L$^{-1}$ of PDO, a yield up to 0.53 g·g$^{-1}$ and productivity up to 3.18 g·L$^{-1}$·h$^{-1}$ whereas isolated clone was able to produce PDO in medium containing around 105 g·L$^{-1}$ of glycerol contained in industrial glycerine with a titer up to 51.30 g/L$^{-1}$ of PDO, a yield up to 0.50 g·g$^{-1}$ and productivity up to 3.05 g·L$^{-1}$·h$^{-1}$.

In the present patent application, the inventors have noticed that a co-culture of the population of *C. acetobutylicum* DG1 pSPD5 adapted strains with different microorganisms, so called microbial consortium, provides an improved production of PDO with a higher titer of PDO, better yield and less residual glycerol compared to the performances of the population of *C. acetobutylicum* DG1 pSPD5 adapted strains without microbial consortium. In particular, this microbial consortium is able to produce PDO at this improved level in presence of high concentration of glycerol contained in industrial glycerine (up to 105 g·L$^{-1}$ of glycerol from industrial glycerine). Thus using the co-culture of the invention allows a better production of PDO but also an easier purification process since residual glycerol is decreased with the co-culture compared with just *C. acetobutylicum* DG1 pSPD5 adapted strains without microbial consortium.

BRIEF DESCRIPTION OF THE INVENTION

The present invention concerns a microbial consortium comprising at least one strain *Clostridium acetobutylicum* and at least one strain chosen among strains of *Clostridium sporogenes* and/or strains of *Clostridium sphenoides*.

Particularly, the microbial consortium according to the present invention comprised at least 85% of *C. acetobutylicum*, less than 0.2% of *C. sporogenes* and preferably from 0.001% to 0.2% of *C. sporogenes*, and/or less than 15% of *C. sphenoides* and preferably from 0.1% to 15% of *C. sphenoides*.

In a particular embodiment of the invention, in the microbial consortium according to the present invention, the strain *C. acetobutylicum* is adapted for growth and production of 1,3-propanediol from a culture medium with high glycerol content and specifically with a high concentration of glycerol originating from industrial glycerine.

The microbial consortium of the invention comprising at least one strain *C. acetobutylicum* and at least one strain of *C. sporogenes*, or comprising at least one strain *C. acetobutylicum* and at least one strain of *C. sphenoides*, may be named as a co-culture, and in these cases the co-culture preferably comprises a strain *C. acetobutylicum* which is previously adapted for growth and production of 1,3-propanediol from a culture medium with high glycerol content and specifically with a high concentration of glycerol contained in industrial glycerine.

The present invention also concerns a method for the production of 1,3-propanediol, comprising culturing the microbial consortium according to the invention in a culture medium comprising glycerol as sole source of carbon, and recovering the 1,3-propanediol produced from the culture medium.

Furthermore, the present invention relates to the use of at least one strain *C. sporogenes* and/or at least one strain *C. sphenoides* for improving the production of 1,3-propanediol, more particularly for improving the yield and the titer of PDO, from a fermentative process by co-culturing with at least one strain *C. acetobutylicum* in a culture medium containing a high concentration of glycerol as sole source of carbon.

Particularly, the at least one strain *C. sporogenes* and/or at least one strain *C. sphenoides* is/are used as a co-culture in a fermentative process for the production of PDO with at least one strain *C. acetobutylicum* which is already adapted for growth and production of PDO in a culture medium containing a high concentration of glycerol as sole source of carbon.

DETAILED DESCRIPTION OF THE INVENTION

The terms "microbial consortium" or "co-culture" are used interchangeably to denote the use of two or more microbial species in the fermentation process.

In a first aspect, the present invention concerns a microbial consortium comprising at least one strain *C. acetobutylicum* and at least one strain chosen among strains of *C. sporogenes* and/or strains of *C. sphenoides*.

The microbial consortium according to the invention is a combination of several *Clostridia* strains, the majority of which belonging to the species *Clostridium acetobutylicum*.

In an advantageous embodiment, the microbial consortium of the invention comprises at least one strain *C. acetobutylicum*, at least one strain *C. sporogenes* and/or at least one strain *C. sphenoides*. More preferably, the microbial consortium of the invention comprises at least one strain *C. acetobutylicum*, at least one strain *C. sporogenes* and at least one strain *C. sphenoides*.

Particularly, the microbial consortium according to the present invention comprises at least 85% of *C. acetobutylicum*, from 0.001% to 0.2% of *C. sporogenes*, and/or from 0.1% to 15% of *C. sphenoides* considering that the totality of the cells contained in the culture corresponds to 100%.

In a preferred embodiment, the microbial consortium comprises from 85% to 99.8% of *C. acetobutylicum*, from 0.001% to 0.15% of *C. sporogenes* and/or from 0.2% to 15% of *C. sphenoides*.

In a more preferred embodiment, the microbial consortium comprises from 90% to 99.8% of *C. acetobutylicum*, from 0.002% to 0.13% of *C. sporogenes* and/or from 0.2% to 10% of *C. sphenoides*.

In a more preferred embodiment, the microbial consortium of the invention consists of at least one strain *C. acetobutylicum* and at least one strain *C. sphenoides*. Even more preferably the microbial consortium of the invention consists of at least one strain *C. acetobutylicum*, at least one strain *C. sphenoides* and at least one strain *C. sporogenes*. According to these specific embodiments, the respective percentages of each of the *Clostridia* mentioned above also apply mutatis mutandis.

In an advantageous embodiment, the microbial consortium according to the present invention is useful for and allows the production of 1,3-propanediol when culturing in an appropriate culture medium with high glycerol content.

Therefore, in a specific embodiment, in the microbial consortium of the present invention the strain *C. acetobutylicum* is adapted for growth and production of 1,3-propanediol from a culture medium with high glycerol content and specifically with a high concentration of glycerol contained in industrial glycerine.

A "*C. acetobutylicum* adapted", "*C. acetobutylicum* previously adapted", or "*C. acetobutylicum* being adapted" means a *C. acetobutylicum* which is modified to be able to grow on high concentration of industrial glycerine.

Method for directing the glycerol metabolism towards production of 1,3-propanediol are known in the art (see for instance WO 2006/128381, Gonzalez-Pajuelo & al. 2006).

For example, the *C. acetobutylicum* strain may be adapted to grow in a culture medium with high glycerol content and specifically with a high concentration of glycerol originating from industrial glycerine by a selection pressure culturing process as disclosed in WO 2010/128070 patent application.

Also as for example, strains of *C. acetobutylicum* genetically modified for the production of 1,3-propanediol from glycerol as sole source of carbon are known in the art and disclosed, particularly in applications WO 2001/04324 and WO 2010/128070.

The expression "genetically modified" means that the strain has been transformed in the aim to change its genetic characteristics. Endogenous genes can be attenuated, deleted, or over-expressed, or preferably exogenous genes can be introduced, carried by a plasmid, or integrated into the genome of the strain, to be expressed into the cell.

The term "plasmid" or "vector" as used herein refers to an extra chromosomal element often carrying genes which are not part of the central metabolism of the cell, and usually in the form of circular double-stranded DNA molecules.

Any standard techniques of mutagenesis and/or gene replacement in *Clostridium*, such as disclosed in application WO 2008/040387 which contents are incorporated herein by reference, may be used for adapting the *C. acetobutylicum* strain for growth and production of 1,3-propanediol from a culture medium with high glycerol content and specifically with a high concentration of glycerol originating from industrial glycerine.

The adaptation of the strain *C. acetobutylicum* is preferably carried out by an anaerobic continuous process which is a technique well known by the skilled person. Among the particulars of this process known by the one skilled in the art, it may be for example mentioned that fed medium is added to the fermenter continuously and an equivalent amount of converted nutrient solution with microorganisms is simultaneously removed from the system. The rate of nutrient exchange is expressed as the dilution rate. Hence the dilution rate is applied to the culture medium, takes into consideration maximum growth rate of the microorganism and impacts the rate of intake and withdrawal of the medium.

The continuous process for the adaptation of the strain *C. acetobutylicum* is preferably carried out in anaerobic conditions.

The man skilled in the art knows how to manage each of these experimental conditions, and to define the culture conditions for the *Clostridia* strains used according to the invention. In particular *Clostridia* strains are fermented at a temperature between 20° C. and 60° C., preferentially between 25° C. and 40° C. for *C. acetobutylicum*.

In a preferred embodiment, in the microbial consortium of the invention, the strain *C. acetobutylicum* is previously adapted, preferably by an anaerobic continuous process, for growth and production of 1,3-propanediol from a culture medium with high glycerol content presenting an increased flux of 1,3-propanediol production by introducing extra copies of the 1,3-propanediol operon from *C. butyricum* encoding enzymes involved in the vitamin B12-independent 1,3-propanediol pathway. In particular, the 1,3-propanediol operon from *C. butyricum* is either over-expressed by a plasmid or integrated into the chromosome of the strain *C. acetobutylicum* to be adapted. For example, the pSPD5 plasmid can be used for an over-expression of the 1,3-propanediol operon (Gonzalez-Pajuelo et al., 2006).

In an advantageous embodiment, in the microbial consortium of the invention, the strain *C. acetobutylicum* is previously adapted for growth and production of 1,3-propanediol during a continuous culture process in which the fed medium contains a concentration of glycerol originating from industrial glycerine comprised between 90 and 120 g/L, and preferably of about 105 g/L.

Said "adaptation" of the producing microorganism is obtained by culturing the microorganism on a culture medium comprising high industrial glycerine content at a low dilution rate, and selecting the adapted microorganism able to grow on the culture medium having high concentration of glycerol originating from industrial glycerine.

To this end, the strain *C. acetobutylicum* is advantageously cultured at a low dilution rate over a period ranging from 24 hours to 10 days, preferably more than 2 days, more preferably about 8 days.

The dilution rate is generally comprised between 0.005 and 0.1 $h^{-1}$, preferably between 0.005 and 0.02 $h^{-1}$. The dilution rate can be changed during the adaptation method, eventually with a first step comprised between 0.005 and 0.02 $h^{-1}$ and a second step where the dilution rate is increased up to 0.1 $h^{-1}$, more preferably 0.07 $h^{-1}$. When the dilution rate is modified during the adaptation method, dilution rate between 0.005 and 0.02 $h^{-1}$ are called "low dilution rate" while dilution rate between 0.02 and 0.1 $h^{-1}$ are common dilution rate.

In a specific embodiment of the invention, the strain *C. acetobutylicum* to be adapted is cultivated in continuous culture using a fed medium containing between 90 and 120 g/L of glycerol and preferably of about 105 $g \cdot L^{-1}$ of raw glycerol, at a low dilution rate comprised between 0.005 and 0.02 $h^{-1}$, preferably 0.02 $h^{-1}$. Over a period of maximum 10 days, preferably between 5 and 8 days, the strain *C. acetobutylicum* is adapted to the high glycerine concentration present in the fed medium, and the dilution rate can be increased up to 0.1 $h^{-1}$, preferably up to 0.07 $h^{-1}$.

Preferably, the strain *C. acetobutylicum* is previously adapted by the process described in WO 2010/128070 and WO 2012/062832.

The microbial consortium of the invention comprising at least one strain *C. acetobutylicum* and at least one strain of *C. sporogenes*, or comprising at least one strain *C. acetobutylicum* and at least one strain of *C. sphenoides*, the microbial consortium may be named as a co-culture, and in these cases the co-culture preferably comprises a strain *C. acetobutylicum* which is previously adapted for growth and production of 1,3-propanediol from a culture medium with high glycerol content and specifically with a high concentration of glycerol contained in industrial glycerine. All the preferred embodiment concerning the strain *C. acetobutylicum* adapted for growth and production of 1,3-propanediol from a culture medium with high glycerine content and specifically with a high concentration of glycerol originating from industrial glycerine mentioned above also apply mutatis mutandis to this specific embodiment.

A co-culture comprising or consisting of at least one strain *C. acetobutylicum* and at least one strain of *C. sporogenes* or a co-culture comprising or consisting of at least one strain *C. acetobutylicum* and at least one strain of *C. sphenoides*, including all the preferred embodiments described above, are also aspects of the present invention.

In another aspect, the present invention relates to a method for the production of 1,3-propanediol in a continuous fermentation process of glycerol, comprising culturing a microbial consortium according to the invention in a fed medium comprising glycerol as sole source of carbon, and recovering the 1,3-propanediol produced from the culture medium.

An "appropriate culture medium" or a "culture medium" refers to a culture medium optimized for the growth and the diol-production of the *Clostridium* strains. The fermentation process is generally conducted in reactors with a synthetic, particularly inorganic, culture medium of known defined composition adapted to the *Clostridium* species used and containing glycerine.

The terms "glycerine" refers to the solution containing the glycerol molecule.

In a particular embodiment, glycerol is added to the culture medium in the form of glycerine composition comprising at least 50% of glycerol, preferably at least 85% of glycerol.

Advantageously, the glycerine used in the culture medium of the invention is industrial glycerine. "Industrial glycerine" means a glycerine product obtained from an industrial process without substantial purification. Industrial glycerine can also be designated as "raw glycerine". Industrial glycerine comprises more than 70% of glycerol, preferably more than 80%, water and impurities such as methanol, mineral salts or fatty acids. The maximum content of glycerol in industrial glycerine is generally 90%, more generally about 85%.

Industrial processes form which industrial glycerine is obtained are, inter alia, manufacturing methods where fats and oils, particularly fats and oils of plant origin or fats and oils of animal origin or used cooking oils, are processed into industrial products such as detergent or lubricants. In such manufacturing methods, industrial glycerine is considered as a by-product.

In one embodiment, the glycerol used in the method for the production of 1,3-propanediol is provided by industrial glycerine.

In a particular embodiment, the industrial glycerine is a by-product from biodiesel production and comprises known impurities of glycerine obtained from biodiesel production, comprising about 80 to 85% of glycerol with salts, methanol, water and some other organic compounds such as fatty acids. Industrial glycerine obtained from biodiesel production may be further subjected to an acidification step to eliminate fatty acids. The man skilled in the art known technology of acidification and is able to define the best conditions of acidification according to the glycerine used.

The terms "high glycerol content" or "high concentration of glycerol" means more than 90 $g \cdot L^{-1}$ of glycerol in the fed medium. In preferred embodiments, the concentration is comprised between 90 and 200 $g \cdot L^{-1}$ of glycerol, more particularly between 90 and 140 g/L of glycerol, preferably about 120 $g \cdot L^{-1}$ of glycerol and more preferably about 105 $g \cdot L^{-1}$ of glycerol contained into the glycerine solution.

In a preferred embodiment, in the method for the production of 1,3-propanediol of the present invention, the glycerol concentration in the fed medium is comprised between 90 and 120 g/L glycerol, and is preferably about 105 g/L of glycerol contained into the glycerine solution.

In the method of the present invention, the production of 1,3-propanediol is preferably carried out by an anaerobic continuous fermentation process by culturing the microbial consortium or co-culture of the invention described above in a culture medium comprising glycerol as sole source of carbon, said culture medium being a minimal medium without addition of organic nitrogen.

The term "minimal medium" means a culture medium strictly mineral comprising a chemically defined composition on which organisms are grown apart from the glycerine solution.

Such culture media are disclosed in the art, particularly in WO 2010/128070 filed on May 5, 2010 and WO 2011/042434 filed on May 10, 2010, which contents are incorporated herein by reference.

In a preferred embodiment, the 1,3-propanediol thus obtained from the method according to the invention is further purified.

Methods for recovering and eventually purifying 1,3-propanediol from a fermentation medium are known to the skilled person. 1,3-propanediol may be isolated by distillation. In most embodiments, 1,3-propanediol is distilled from the fermentation medium with a by-product, such as acetate, and then further purified by known methods.

A particular preferred purification method is disclosed in applications WO 2009/068110 and WO 2010/037843, which content is incorporated herein by reference.

In another aspect, the present invention relates to the use of at least one strain C. sporogenes and/or at least one strain C. sphenoides for improving the production of 1,3-propanediol, in particular the yield and the titer of PDO, from fermentative process by co-culturing with at least one strain C. acetobutylicum in a culture medium containing a high concentration of glycerol as sole source of carbon.

Preferably, the use according to the invention is of at least one strain C. sporogenes and/or at least one strain C. sphenoides to at least one strain C. acetobutylicum, and more preferably to at least one strain C. acetobutylicum adapted for growth and production of 1,3-propanediol from a culture medium with high glycerol content and specifically with a high concentration of glycerol originating from industrial glycerine. Concerning the strain C. acetobutylicum adapted for growth and production of 1,3-propanediol from a culture medium with high glycerine content, all the above preferred embodiments apply mutatis mutandis for this aspect of the invention relating to the use of improving the production of 1,3-propanediol and in particular the yield and the titer of 1,3-propanediol, from fermentative process.

The method and the use according to the present invention, in its different embodiments, leads to production of 1,3-propanediol with a titer up to 52.9 $g \cdot L^{-1}$, a yield up to 0.5 $g \cdot g^{-1}$ and a productivity up to 3.65 $g \cdot L^{-1} \cdot h^{-1}$ for a dilution rate of 0.069 $h^1$.

EXAMPLES

The methods and systems disclosed herein are further illustrated in the following examples, which are provided by way of illustration and are not intended to be limiting.

A person skilled in the art will appreciate the applicability and the necessary modifications to adapt the features described in the present section. Alternatively, the methods could be performed with other standard methods known to those skilled in the art.

Protocols

Culture Media and Conditions

The media and the conditions used for cultures were already described in patent application WO 2010/128070:
flask cultures: synthetic and rich (CGM: Clostridial Growth Medium) media
anaerobic continuous culture DNA Isolation Genomic DNA was extracted from 1 ml of culture, homogenized and transferred to 2 ml tube with Glass Bead Tube Kit, 0.1 mm, using a Precellys®24 lyser/homogeniser (Bertin Technologies, Saint Quentin Yvelines, France). Precellys®24 settings were: 6500 rpm, 20 sec cycle duration, 5 sec delay time between cycles, for 2 total cycles. After Precellys extraction, the lysate was centrifuged at 10,000 g for 10 min and the supernatant used for total genomic extraction using the NucleoSpin® Gel and PCR Clean-up from Macherey (Macherey Nagel, Hoerdt, France).

Quantification of a Specific Desoxyribonucleic Acid Sequence from a Specific Microorganism by Quantitative PCR The recent advances in molecular techniques such as PCR technology enable rapid, specific, and sensitive detection and the identification of potential microorganisms in different type of environments as for instance in this patent application, culture broth from a fermentative production.

Absolute quantification in samples was determined by quantitative PCR (qPCR) using the Sso Advanced Universal SYBR Green Supermix (Bio-rad Mitry Mory, France). The qPCR was performed on a Bio-Rad C1000™ Thermal Cycler equipped with a CFX96™ Real-Time System (Bio-Rad Mitry Mory, France).

Reactions mixtures consisted of 1×Sso Advanced Universal SYBR Green Supermix (Bio-Rad Mitry Mory, France), 6 µL of each forward (F) and reverse (R) primers (1 µM), 2 µL of diluted sample (2 ng/µL from Nanodrop measure) and nuclease free water to reach a final volume of 20 µL. Amplification was achieved according to the following thermal cycling program: initial melting at 98° C. for 2 min. (1 cycle) followed by 40 cycles of melting at 98° C. for 10 sec, annealing of primers and elongation at 60° C. for 30 sec. (Melt Curve 65 to 95° C., increment 0.5° C. every 5 sec).

A standard curve was determined for each microorganism using Cq values of serial dilutions of genomic DNA at known concentrations. The Cq value for each well (standard curve and samples) was determined by the CFX Manager™ 3.1 software. The samples were plotted against the standard curve to determine abundance of nucleic acid. Absolute quantifications were based on one gapC gene copy per cell for *C. acetobutylicum*, one cpn60 gene copy per cell for *C. sphenoides* and one tpi gene copy per cell for *C. sporogenes*. For the purposes of calculation, nucleic acid extractions were assumed to be perfect, because no measurement of extraction efficiency is available.

Microbial *C. acetobutylicum* population overexpressing the 1.3-propanediol operon from *C. butyricum* and adapted for growth and production of 1.3-propanediol from a culture medium with a high concentration of industrial glycerine as described in patent application WO2012062832A1 was named "Type 174P population" and used herein as the reference.

In this patent application, microbial consortium comprising the "Type 174P population" and other microorganisms *C. sphenoides* and *C. sporogenes*, was used to improve the production of 1.3-propanediol from a culture medium with high glycerine content. This microbial consortium was named "Type 192P microbial consortium".

Example 1: Performances of "Type 174P Population" and "Type 192P Microbial Consortium" in a Chemostat by Continuous Culture with High Concentrations of Raw Glycerine Bacterial Strains:
 Type 174P population: population of *C. acetobutylicum* strain DG1 pSPD5 PD0001VE05 evolved on high concentrations of raw glycerine
 Type 192P microbial consortium: consortium of Type 174P population and other microorganisms *C. sphenoides* and *C. sporogenes*.

Culture Media:
The synthetic media used for clostridia batch cultivations contained per liter of tap water: glycerol, 30 g; $KH_2PO_4$, 0.5 g; $K_2HPO_4$, 0.5 g; $MgSO_4$, $7H_2O$, 0.2 g; $CoCl_2$ $6H_2O$, 0.01 g; $H_2SO_4$, 0.1 ml; $NH_4Cl$, 1.5 g; biotin, 0.16 mg; p-amino benzoic acid, 32 mg and $FeSO_4$, $7H_2O$, 0.028 g. The pH of the medium was adjusted to 6.3 with $NH_4OH$ 3N. Commercial glycerol purchased from SDS Carlo_Erba (purity 99%) was used for batch cultivation. The feed medium for continuous cultures contained per liter of tap water: glycerol from raw glycerine, 105 g; $KH_2PO_4$, 0.45 g; $K_2HPO_4$, 0.45 g; $MgSO_4$, $7H_2O$, 0.2 g; $CoCl_2$ $6H_2O$, 0.013 g; biotin, 0.08 mg; p-amino benzoic acid, 16 mg; $FeSO_4$, $7H_2O$, 0.04 g; anti-foam, 0.05 ml; $ZnSO_4$, $7H_2O$, 8 mg; $CuCl_2$, $2H_2O$, 4 mg; $MnSO_4$, $H_2O$, 20 mg. Medium pH was adjusted between 3.5 and 4 with $H_2SO_4$ 96%. Raw glycerine, from the transesterification process for biodiesel, was provided by different providers (Novance, ADM, Diester Industries, Greenergy, Carotech Berhad) and had purity comprised between 80 and 86% (w/w). These glycerines were blended and pretreated by acidification.

Experimental Set-Up:
Continuous cultures were performed in a 5 L bioreactor Tryton (Pierre Guerin, France) with a working volume of 2000 mL. The culture volume was kept constant at 2000 mL by automatic regulation of the culture level. Cultures were stirred at 200 RPM, the temperature was set to 35° C. and pH maintained constant at 6.5 by automatic addition of $NH_4OH$ 5.5 N. To create anaerobic conditions, the sterilized medium in the vessel was flushed with sterile $O_2$-free nitrogen for one hour at 60° C. and flushed again until 35° C. was attained (flushing during 2 hours). The bioreactor gas outlet was protected from oxygen by a pyrogallol arrangement (Vasconcelos et al, 1994). After sterilization the feed medium was also flushed with sterile $O_2$-free nitrogen until room temperature was attained and maintained under nitrogen to avoid $O_2$ entry.

Batch and Continuous Cultures Process:
The process used to evaluate has been described in patent application WO 2010/128070 (example 2).

A culture growing in a 100 mL Penicillin flask on synthetic medium (the same as described above for batch culture but with addition of acetic acid, 2.2 $g·L^{-1}$ and MOPS, 23.03 $g·L^{-1}$) taken at the end of exponential growth phase was used as inoculum (5% v/v). Cultures were first grown batchwise. At the early exponential growth phase we performed a pulse of glycerol from raw glycerine: For the pulse, synthetic medium (the same as described for feed culture) with 105 $g·L^{-1}$ of glycerol from raw glycerine was added at a static flow rate during 3 hours (i.e. addition of 18 $g·L^{-1}$ of glycerol). Then the growth continued batchwise and before the end of the exponential growth phase the continuous feeding started with a dilution rate of 0.035 $h^{-1}$: The feed medium contains 105 $g·L^{-1}$ of glycerol from raw glycerine. 6-8 days after inoculation of the bioreactor and after 4 residence times (RT) the dilution rate was increased from 0.035 $h^{-1}$ to 0.070 $h^{-1}$ in five days. After that, stabilization of the culture was followed by 1,3-propanediol production and glycerol consumption using the HPLC protocol described below. Particularly we waited until the concentration of residual glycerine was as low as possible. The overall performances of Type 192P microbial consortium are presented in Table 1 and compared with performances of the Type 174P population containing exclusively *C. acetobutylicum* strain DG1 pSPD5 PD0001VE05 evolved on high concentrations of raw glycerine under the same conditions.

Analytical Procedures:
Cell concentration was measured turbidimetrically at 620 nm and correlated with cell dry weight determined directly. Glycerol, 1,3-propanediol, ethanol, lactate, acetic and butyric acids concentrations were determined by HPLC analysis. Separation was performed on a Biorad Aminex HPX-87H column and detection was achieved by refractive index. Operating conditions were as follows: mobile phase sulphuric acid 0.5 mM; flow rate 0.5 ml/min, temperature, 25° C.

TABLE 1

Performances of the *C. acetobutylicum* Type 174P population and of the Type 192P microbial consortium grown in continuous culture (mean data from respectively 20 and 19 chemostats). The feed medium contained 105 g · $L^{-1}$ of glycerol from raw glycerine, dilution rate was 0.035 $h^{-1}$ and 0.070 $h^{-1}$. Values correspond to the average of samples analyzed after at least 9 residences times at dilution rate of 0.070 $h^{-1}$.

|  | PDO Production performances for Type 174P population | PDO production performances for Type 192P microbial consortium |
|---|---|---|
| Feed glycerine (g · $l^{-1}$) | 106 | 105 |
| 1,3-propanediol (g · $l^{-1}$) | 51.5 | 52.9 |
| Y1,3-PDO (g · $g^{-1}$) | 0.49 | 0.50 |

TABLE 1-continued

Performances of the *C. acetobutylicum* Type 174P population and of the Type 192P microbial consortium grown in continuous culture (mean data from respectively 20 and 19 chemostats). The feed medium contained 105 g · L$^{-1}$ of glycerol from raw glycerine, dilution rate was 0.035 h$^{-1}$ and 0.070 h$^{-1}$. Values correspond to the average of samples analyzed after at least 9 residences times at dilution rate of 0.070 h$^{-1}$.

| | PDO Production performances for Type 174P population | PDO production performances for Type 192P microbial consortium |
|---|---|---|
| Q1,3PDO (q · l$^{-1}$ · h$^{-1}$) | 3.66 | 3.65 |
| Dilution rate (h$^{-1}$) | 0.071 | 0.069 |
| Residual glycerine (g · l$^{-1}$) | 4.1 | 1.2 |
| Biomass (g · l$^{-1}$) | 2.6 | 2.7 |
| Acetic acid (g · l$^{-1}$) | 1.8 | 2.0 |
| Butyric acid (g · l$^{-1}$) | 11.6 | 11.9 |

Y1,3-PDO: PDO yield (g/g of glycerolengaged)
Q1,3PDO: PDO volumetric productivity These results show that the Type 192P microbial consortium exhibits better results on PDO production than the Type 174P population (higher titer and yield of PDO and less residual glycerine).

Example 2: Microbial Consortium Quantification

Abundance of each microorganism in samples was determined by quantitative PCR (qPCR) using the Sso Advanced Universal SYBR Green Supermix (Bio-rad Mitry Mory, France) on a Bio-Rad C1000™ Thermal Cycler equipped with a CFX96™ Real-Time System (described in Protocols). The gapC gene based primers used to target *C. acetobutylicum* were gapC_F, 5'-TGCTGCTGTAAGTATCATC-3' (SEQ ID NO: 1) and gapC_R, 5'-GTTGGAACTGGAACTCTT-3' (SEQ ID NO: 2). The cpn60 gene based primers used to target *C. sphenoides* were cpn60_F, 5'-TTATATGTGCACCGATATG-3' (SEQ ID NO: 3) and cpn60_R, 5'-GAGAAGTCTTGCGCCGGAC-3' (SEQ ID NO: 4). The tpi gene based primers used to target *C. sporogenes* were tpi_F, 5'-CCAGCGGTATTAGAAGAA-3' (SEQ ID NO: 5) and tpi_R, 5'-GTCCTATAATTACATAATGAACTC-3' (SEQ ID NO: 6).

In the two tables below, are given percentages of representation of the different species present in the cultures of Type 174P population and of Type 192P microbial consortium considering that the totality of the cells contained in each culture corresponds to 100%.

TABLE 2

"Type 174P population" composition at different steps of the culture

| Samples | *C. acetobutylicum* | *C. sphenoïdes* | *C. sporogenes* |
|---|---|---|---|
| Beginning of chemostat phase, 0.5 RT, D = 0.035 h−1 | 100% | 0% | 0% |
| Before increasing flow rate, 3.8 RT, D = 0.035 h−1 | 100% | 0% | 0% |
| Feed culture, D = 0.045 h$^{-1}$ | 100% | 0% | 0% |
| Established permanent state culture | 100% | 0% | 0% |

The "Type 174P population" fermentation for 1,3-propandiol production does not contain any *C. sphenoides* or *C. sporogenes* bacteria. This population is not a consortium.

TABLE 3

"Type 192P microbial consortium" composition at different steps of the culture. Different trials were realized and minimal and maximal proportions obtained are indicated.

| Samples | *C. acetobutylicum* | *C. sphenoïdes* | *C. sporogenes* |
|---|---|---|---|
| Beginning of chemostat phase, 0.5 RT, D = 0.035 h$^{-1}$ | 90.24%-96.06% | 3.92%-9.76% | 0.002%-0.02% |
| Before increasing flow rate, 3.8 RT, D = 0.035 h$^{-1}$ | 90.79%-99.57% | 0.4%-9.18% | 0.03%-0.12% |
| Feed culture, D = 0.045 h$^{-1}$ | 92.24%-99.76% | 0.21%-7.73% | 0.03%-0.13% |
| Established permanent state culture | 96.34%-98.22% | 1.76%-3.63% | 0.03%-0.11% |

On the contrary, table 3 above shows that *C. sphenoides* and *C. sporogenes* bacteria are present in the "Type 192P microbial consortium" at all the steps of the culture and during the production fermentation. The proportion of each microorganism varied among the continuous culture phases.

According to further experimental trails carried out in the same conditions as defined above, the different species present in the established permanent state culture of "Type 192P microbial consortium" was the following:

| | |
|---|---|
| C. acetobutylicum | 96.34%-98.64% |
| C. sphenoïdes | 1.29%-3.63% |
| C. sporogenes | 0.03%-0.11%. |

Example 3: *C. sphenoides* and *C. sporogenes* Batch Cultures Assay

As a control of the invention, *C. sphenoides* and *C. sporogenes* were together cultivated or independently cultivated in rich medium (CGM: Clostridial Growth Medium as described in Protocols) containing commercial glycerol or glycerol originating from glycerine (30 g/L). Despite the microorganisms' growth, no glycerol/glycerine was consumed and no 1.3-propanediol was produced.
Otherwise, several assays were made to grow *C. sphenoides* or *C. sporogenes* or *C. sphenoides* and *C. sporogenes* in flask cultures containing synthetic minimal media (described in Protocols) with glycerol/glycerine (30 g/L) but no growth was observed.
All these data suggest that neither *C. sphenoides* nor *C. sporogenes* are able to produce 1.3-propanediol from glycerol/glycerine as sole carbon source and that their growth and persistence in the continuous production of 1, 3-propanediol of the "Type 192P microbial consortium" is due somehow to the presence of *C. acetobutylicum*. Moreover, results from examples 1, 2, 3 and 4 showed that *C. sphenoides* and/or *C. sporogenes* play a critical role into the consortium with *C. acetobutylicum* to improve PDO production performances on high concentration of industrial raw glycerine.

REFERENCES

González-Pajuelo M, Meynial-Salles I, Mendes F, Andrade J C, Vasconcelos I, and Soucaille P. 2005. Metabolic engineering of *Clostridium acetobutylicum* for the industrial production of 1,3-propanediol from glycerol. Metabolic Engineering 7: 329-336.

González-Pajuelo M, Meynial-Salles I, Mendes F, Soucaille P. and Vasconcelos I. 2006. Microbial conversion of a natural producer, *Clostridium butyricum* VPI 3266, and an engineered strain, *Clostridium acetobutylicum* DG (pSPD5). Applied and Environmental Microbiology, 72: 96-101.

Papanikolaou S, Ruiz-Sanchez P, Pariset B, Blanchard F and Fick M. 2000. High production of 1,3-propanediol from industrial glycerol by a newly isolated *Clostridium butyricum* strain. Journal of Biotechnology. 77: 191-208.

Vasconcelos I, Girbal L, Soucaille P. 1994. Regulation of carbon and electron flow in *Clostridium acetobutylicum* grown in chemostat culture at neutral pH on mixtures of glucose and glycerol. Journal of bacteriology. 176(5): 1443-1450.

The invention claimed is:

1. A microbial consortium comprising:

at least one strain of *Clostridium acetobutylicum;* at least one strain *Clostridium sporogenes*, and at least one strain of *Clostridium sphenoides;* wherein the strain of *Clostridium acetobutylicum* is previously adapted for growth and production of 1,3-propanediol from a culture medium with high glycerol content presenting an increased flux of 1,3-propanediol production by introducing extra copies of the 1,3-propanediol operon from *Clostridium butyricum* encoding enzymes involved in the vitamin B12-independent 1,3-propanediol pathway.

2. The microbial consortium according to claim 1 comprising at least 85% of *C. acetobutylicum*, from 0.001% to 0.2% of *C. sporogenes*, and from 0.1% to 15% of *C. sphenoides.*

3. The microbial consortium according to claim 1 comprising from 85% to 99.8% of *C. acetobutylicum*, from 0.001% to 0.15% of *C. sporogenes*, and from 0.2% to 15% of *C. sphenoides.*

4. The microbial consortium according to claim 1 comprising from 90% to 99.8% of *C. acetobutylicum*, from 0.002% to 0.13% of *C. sporogenes*, and from 0.2% to 10% of *C. sphenoides.*

5. The microbial consortium according to claim 1 consisting of at least one strain of *C. acetobutylicum*, at least one strain of *C. sporogenes*, and at least one strain of *C. sphenoides.*

6. The microbial consortium according to claim 1 wherein the strain of *C. acetobutylicum* is adapted for growth and production of 1,3-propanediol from a culture medium with high glycerol content and specifically with a high concentration of glycerol originating from industrial glycerine.

7. The microbial consortium according to claim 1, wherein said *C. acetobutylicum* is previously adapted for growth and production of 1,3-propanediol during a continuous culture process in which the fed medium contains a concentration of glycerol originating from industrial glycerine comprised between 90 and 120 g/L of glycerol.

8. A method for the production of 1,3-propanediol in a continuous fermentation process of glycerine, comprising culturing a microbial consortium according to claim 1 in a fed medium comprising glycerol as sole source of carbon, and recovering the 1,3-propanediol produced from the culture medium.

9. The method according to claim 8, wherein the glycerine concentration in the fed medium is comprised between 90 and 120 g/L glycerol contained in the glycerine solution.

10. The method according to claim 8, wherein the culture medium is a minimal medium, without addition of organic nitrogen.

11. The method according to claim 8, wherein the 1,3-propanediol is further purified.

12. A method for improving the production of 1,3-propanediol from fermentative process by co-culturing at least one strain of *C. acetobutylicum* with at least one strain of *C. sporogenes* and at least one strain of *C. sphenoides* in a culture medium containing a high concentration of glycerol as sole source of carbon, wherein the strain of *Clostridium acetobutylicum* is previously adapted for growth and production of 1,3-propanediol from a culture medium with high glycerol content presenting an increased flux of 1,3-propanediol production by introducing extra copies of the 1,3-propanediol operon from *Clostridium butyricum* encoding enzymes involved in the vitamin B12-independent 1,3-propanediol pathway.

13. The microbial consortium according to claim 7, wherein the concentration of glycerol originating from industrial glycerine is about 105 g/L.

14. The method according to claim 9, wherein the glycerine concentration in the fed medium is about 105 g/L glycerol contained in the glycerine solution.

* * * * *

```
SEQUENCE LISTING

<160> NUMBER OF SEQ ID NOS: 6

<210> SEQ ID NO 1
<211> LENGTH: 19
<212> TYPE: DNA
<213> ORGANISM: artificial sequence
<220> FEATURE:
<223> OTHER INFORMATION: gapC_F primer

<400> SEQUENCE: 1
tgctgctgta agtatcatc                                                    19

<210> SEQ ID NO 2
<211> LENGTH: 18
<212> TYPE: DNA
<213> ORGANISM: artificial sequence
<220> FEATURE:
<223> OTHER INFORMATION: gapC_R primer

<400> SEQUENCE: 2
gttggaactg gaactctt                                                     18

<210> SEQ ID NO 3
<211> LENGTH: 19
<212> TYPE: DNA
<213> ORGANISM: artificial sequence
<220> FEATURE:
<223> OTHER INFORMATION: cpn60_F primer

<400> SEQUENCE: 3
ttatatgtgc accgatatg                                                    19

<210> SEQ ID NO 4
<211> LENGTH: 19
<212> TYPE: DNA
<213> ORGANISM: artificial sequence
```

-continued

```
<220> FEATURE:
<223> OTHER INFORMATION: cpn60_R primer

<400> SEQUENCE: 4
gagaagtctt gcgccggac                                                   19

<210> SEQ ID NO 5
<211> LENGTH: 18
<212> TYPE: DNA
<213> ORGANISM: artificial sequence
<220> FEATURE:
<223> OTHER INFORMATION: tpi_F primer

<400> SEQUENCE: 5
ccagcggtat tagaagaa                                                    18

<210> SEQ ID NO 6
<211> LENGTH: 24
<212> TYPE: DNA
<213> ORGANISM: artificial sequence
<220> FEATURE:
<223> OTHER INFORMATION: tpi_R primer

<400> SEQUENCE: 6
gtcctataat tacataatga actc                                             24
```